United States Patent
Kinney et al.

(10) Patent No.: US 10,234,424 B2
(45) Date of Patent: Mar. 19, 2019

(54) MAGNETIC PARTICLE INSPECTION TOOL WITH 3D PRINTED MAGNETS

(71) Applicant: Caterpillar Inc., Peoria, IL (US)

(72) Inventors: Christopher Anthony Kinney, Luka, MS (US); Bradley Carl Hill, Dumas, MS (US); Kegan Jon Luick, Corinth, MS (US)

(73) Assignee: Caterpillar Inc., Deerfield, IL (US)

( * ) Notice: Subject to any disclaimer, the term of this patent is extended or adjusted under 35 U.S.C. 154(b) by 148 days.

(21) Appl. No.: 15/380,575

(22) Filed: Dec. 15, 2016

(65) Prior Publication Data

US 2018/0172637 A1    Jun. 21, 2018

(51) Int. Cl.
*H01F 7/02* (2006.01)
*G01N 27/84* (2006.01)

(52) U.S. Cl.
CPC .................. *G01N 27/84* (2013.01)

(58) Field of Classification Search
CPC ...................................... G01N 27/84
USPC ........................................... 335/306
See application file for complete search history.

(56) References Cited

U.S. PATENT DOCUMENTS

| | | | | |
|---|---|---|---|---|
| 2,053,177 | A * | 9/1936 | Bower | B23Q 3/1546 269/8 |
| 2,286,238 | A * | 6/1942 | Simmons | B23Q 3/1546 335/295 |
| 2,319,270 | A * | 5/1943 | Simmons | B23Q 3/1546 269/8 |
| 2,346,193 | A * | 4/1944 | Simmons | B23Q 3/1546 24/303 |
| 3,010,054 | A * | 11/1961 | Goudsmit | B23Q 3/1546 269/8 |
| 3,378,782 | A | 4/1968 | Parker | |
| 3,818,399 | A * | 6/1974 | Edwards | B23Q 3/1546 335/295 |
| 3,855,526 | A | 12/1974 | Molina | |
| 6,357,101 | B1 * | 3/2002 | Sarh | B21J 15/10 29/34 B |

(Continued)

OTHER PUBLICATIONS

Alec Buren, *Revolutionary 3D printed magnets by Polymagnet can change engineering as we know it*, 3ders: 3D Printer and 3D Printing News, Mar. 24, 2016, http://www.3ders.org/articles/20160324-revolutionary-3d-printed-magnets-by-correlated-magnetics-can-change-engineering.html (last visited Dec. 12, 2016).

*Primary Examiner* — Mohamad A Musleh
*Assistant Examiner* — Lisa N Homza
(74) *Attorney, Agent, or Firm* — Finnegan, Henderson, Farabow, Garrett & Dunner, LLP (57) ABSTRACT

A magnetic particle inspection tool is provided including a yoke with an inspection magnet, a first magnetic member, and a second magnetic member. The inspection magnet is configured to magnetize a work piece. The first magnetic member is rotatable relative to the inspection magnet between a first position and a second position, and the inspection magnet is slidable relative to the first magnetic member. The first magnetic member and second magnetic member include a plurality of magnetic sources forming a magnetic surface with a first magnetic pattern and a magnetic surface with a second magnetic pattern. The magnetic surfaces are magnetically attracted when the first magnetic member is in the first position and repelled when in the second position.

12 Claims, 5 Drawing Sheets

(56) References Cited

U.S. PATENT DOCUMENTS

| | | | | |
|---|---|---|---|---|
| 6,621,396 B2* | 9/2003 | Leupold | ............... | H01F 7/0278 |
| | | | | 335/284 |
| 6,652,252 B2* | 11/2003 | Zabar | ................... | F04B 35/045 |
| | | | | 310/12.21 |
| 7,148,776 B2* | 12/2006 | Day | ..................... | B25B 11/002 |
| | | | | 335/289 |
| 7,750,776 B2* | 7/2010 | Honkura | ................... | B22F 3/03 |
| | | | | 310/156.43 |
| 8,179,219 B2 | 5/2012 | Fullerton et al. | | |
| 8,490,955 B2* | 7/2013 | Sarh | ........................ | B21J 15/14 |
| | | | | 269/17 |
| 9,285,345 B2* | 3/2016 | Boenisch | ........... | G01N 27/9033 |
| 2004/0088843 A1* | 5/2004 | Day | ........................ | B21J 15/14 |
| | | | | 29/34 B |
| 2005/0092817 A1* | 5/2005 | Baumann | ............. | B23K 20/126 |
| | | | | 228/212 |
| 2008/0290574 A1* | 11/2008 | Lv | ........................ | B23Q 3/1543 |
| | | | | 269/8 |
| 2012/0146752 A1 | 6/2012 | Fullerton et al. | | |
| 2014/0062241 A1 | 3/2014 | Evans | | |

* cited by examiner

MAGNETIC PARTICLE INSPECTION TOOL WITH 3D PRINTED MAGNETS

TECHNICAL FIELD

The present disclosure relates generally to a magnetic particle inspection tool, and more particularly, to a magnetic particle inspection tool employing 3D printed magnets.

BACKGROUND

Magnetic particle inspection is a non-destructive inspection technique used to detect flaws and defects in a ferromagnetic work piece. The work piece is magnetized using a magnetic inspection tool having two poles. Magnetic particles are sprayed or otherwise distributed across the work piece between the poles after the poles are placed against the work piece. The poles magnetize the work piece and cause the magnetic particles to align and gather within discontinuities along the surface of the work piece. The collection of the magnetic particles indicates a flaw that can be observed with the naked eye. Magnetic particles used in this process may be suspended in a fluid and sprayed on the work piece, and they may also be colored or fluorescent to improve visibility.

Most magnetic inspection tools include a pair of yokes with inspection magnets of opposite polarity. The yokes may include permanent magnetics or electromagnets for magnetizing the work piece. When pressed against the work piece, the yokes are attracted to its ferromagnetic material and induce a magnetic field through the work piece. One problem associated with this process arises when the work piece is located within a larger assembly and within tight confines. Each yoke must be located and affixed to the work piece before spreading the magnetic particles. Therefore, the size of the yoke may be a limiting factor on the ability to position a yoke on certain work pieces. Moreover, once the yoke is affixed to the work piece it is often difficult to remove it. Without sufficient clearance, it may be difficult to obtain the necessary leverage to remove the yoke once affixed to the work piece. Therefore releasing the yoke becomes an issue.

3D printing magnets are a relatively new process in which a plurality of magnetic sources are formed along a surface using a 3D printer to create an array of magnetic sources adjacent to one another. Each magnetic source is a pixel on the surface, each having its own polarity. The arrangement of polarities along the surface forms a magnetic pattern. That pattern can be matched with another printed magnet surface such that the two surfaces can attract or repel each other based on the orientation or rotational position of each. U.S. Patent Application Publication No. US 2012/0146752A1 ("the '752 publication") to Fullerton discloses this 3D printing process.

While the '752 publication describes the 3D printing process generally, the present disclosure is directed to a magnetic particle inspection yoke having 3D printed magnetic members to address the one or more of the problems set forth above and in the prior art.

SUMMARY OF THE INVENTION

In an aspect, the present disclosure is directed to a magnetic particle inspection tool with a yoke including an inspection magnet and a first magnetic member. The inspection magnet is configured to magnetize a work piece when a first surface is attached to the work piece. The first magnetic member is rotatable relative to the inspection magnet between a first position and a second position. The inspection magnet is slidable relative to the first magnetic member, where the first magnetic member includes a plurality of magnetic sources forming a magnetic surface with a first magnetic pattern thereon. A second magnetic member is affixed to a second surface of the inspection magnet and includes a plurality of magnetic sources forming a magnetic surface with a second magnetic pattern thereon. The magnetic surface of the second magnetic member is magnetically attracted to the magnetic surface of the first magnetic member when the first magnetic member is in the first position, and repelled when the first magnetic member is in the second position.

DETAILED DESCRIPTION

Figure 1:
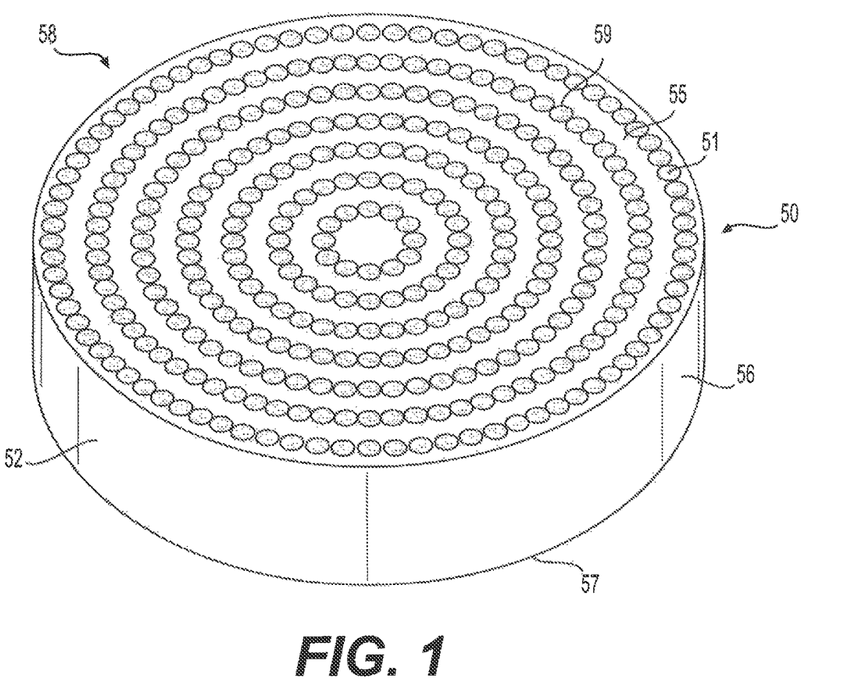
FIG. 1 is a perspective view of an exemplary first magnetic member of the present disclosure.
Figure 2:
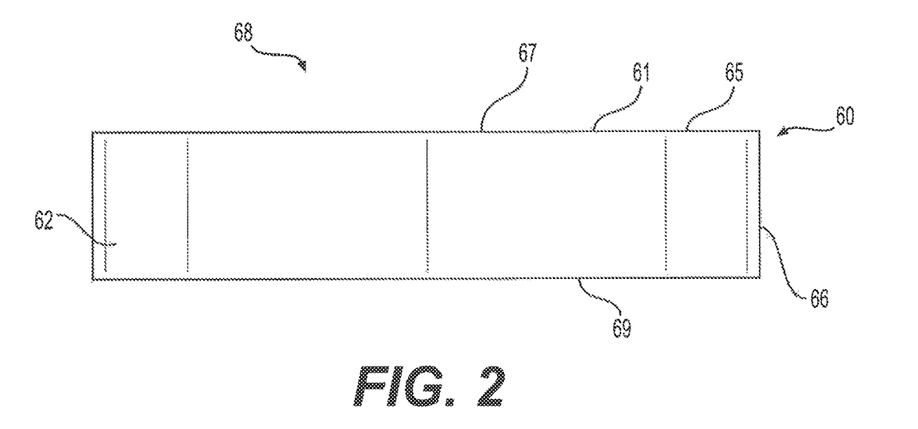
FIG. 2 is a side profile view of the exemplary second magnetic member of the present disclosure.

FIGS. 1 and 2 illustrate an exemplary first magnetic member 50 and second magnetic member 60 of the present disclosure. The first magnetic member 50 and second magnetic member 60 are printed magnets in which a plurality of magnetic sources 51, 61 form the member 50, 60 using a 3D printing process. The magnetic sources 51, 61 form a magnetic surface 55, 65 on each member 50, 60 having a magnetic pattern 58, 68.

Each of the magnetic sources 51, 61 has a polarity along the magnetic surface 55, 65. The arrangement of magnetic sources 51, 61 and their individual polarity along the magnetic surface 55, 65 forms a particular magnetic pattern 58, 68 along each magnetic surface 55, 65. In particular, the magnetic surface 55 of the first magnetic member 50 includes a first magnetic pattern 58. Likewise, the magnetic surface 65 of the second magnetic member 60 includes a second magnetic pattern 68. The arrangement and adjacent polarity of the magnetic sources 51, 61 along each magnetic surface 55, 65 defines the particular magnetic pattern 58, 68 thereon.

As shown in FIGS. 1 and 2, the magnetic sources 51, 61 may form a radial pattern of pixels along each magnetic surface 55, 65. The number of pixels, their density, and their pattern may vary depending on the type of pattern desired and the strength of the magnetic field desired. In an embodiment, the pattern of magnetic sources 51 on the first magnetic member 50 forms a magnetic surface 55 with a first magnetic pattern 58. The magnetic sources 51 may extend through a cross section 52 of the first magnetic member 50 or be printed along the magnetic surface 55.

In addition, the second magnetic member 60 may include a magnetic surface 65 with a second magnetic pattern 68. Again, the magnetic sources 61 may extend through a cross section 62 of the first magnetic member 60 or be printed along the magnetic surface 65. When the magnetic surfaces 55, 65 of the two magnetic members 50, 60 are aligned, they form complimentary patterns 58, 68 such that they attract and repel each other depending on the relative orientation of one magnetic surface to the other.

In an embodiment, the magnetic surface 65 of the second magnetic member 60 is magnetically attracted to the magnetic surface 55 of the first magnetic member 50 when facing each other and when the first magnetic member 50 is rotated into a first position. Moreover, the magnetic surface 65 of the second magnetic member 60 is magnetically repelled from the magnetic surface 55 of the first magnetic member 50 when facing each other and the first magnetic member 50 is rotated into a second position. Therefore, the relative angle of the magnetic surfaces 55, 65 when facing each other (e.g., when parallel) may determine whether they attract or repel.

Figure 3:
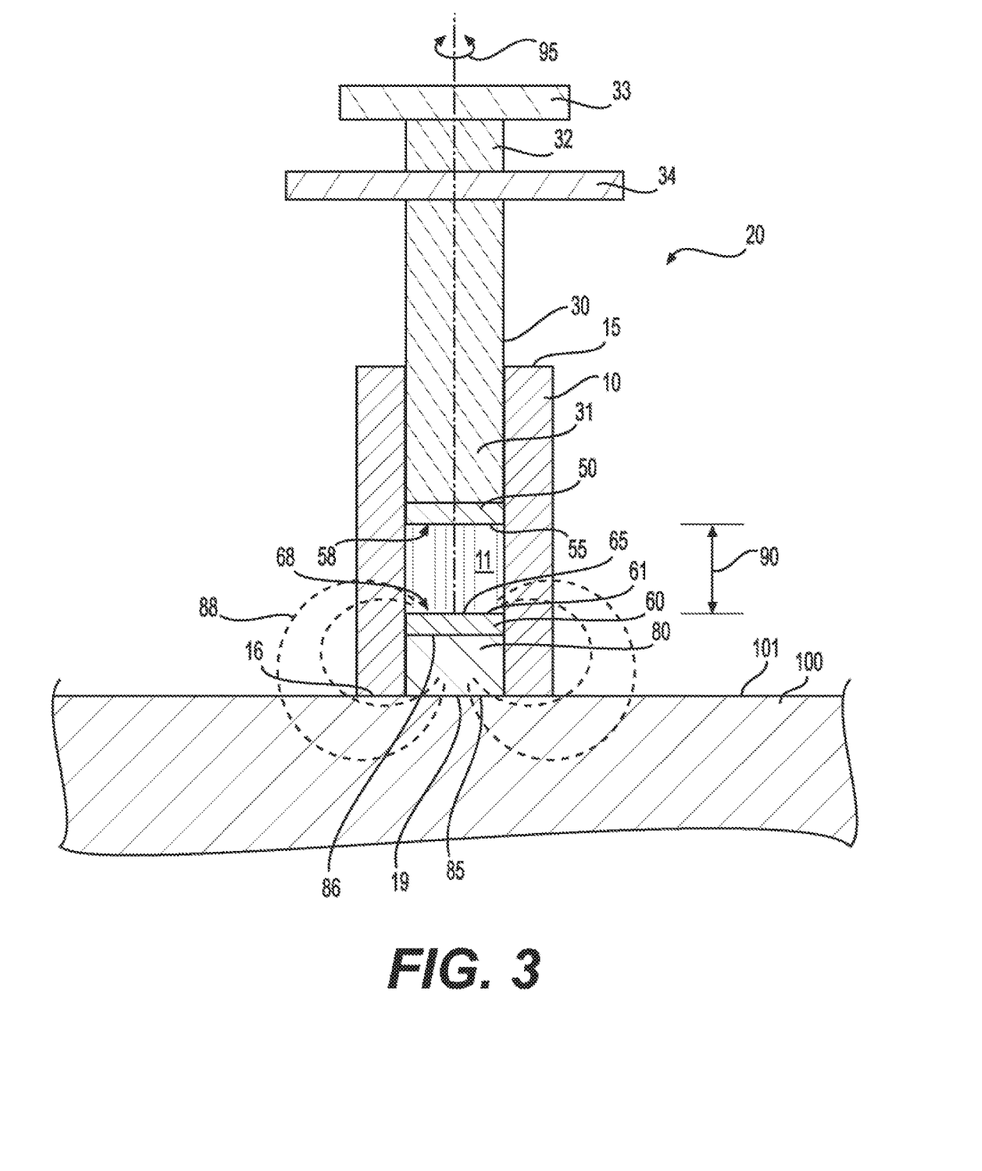
FIG. 3 is a cross-section view of an exemplary yoke of the magnetic particle inspection tool of the present disclosure.

FIGS. 1-3 show an embodiment of the first magnetic member 50, the second magnetic member 60, and an exemplary yoke 20 of the present disclosure. The yoke 20 includes an inspection magnet 80 that may be a permanent magnet. The inspection magnet 80 has a magnetic field 88 that is configured to magnetize a work piece 100 when a first surface 85 of the inspection magnet 80 is attached to a surface 101 of the work piece 100. The magnetic field 88 magnetizes the work piece 100 and the first surface 85 of the inspection magnet 80 is affixed to the surface 101 of the work piece 100 via magnetic attraction.

Removing the inspection magnet 80 from the work piece 100 requires overcoming the magnetic attraction between the inspection magnet 80 and the work piece 100. In an embodiment, the yoke 20 includes the first magnetic member 50, the second magnetic member 60, and the inspection magnet 80. The first magnetic member 50 is rotatable relative to the inspection magnet 80 and the second magnetic member 60. Specifically, the first magnetic member 50 may be rotatable in a first direction 95 between a first position and a second position relative to the inspection magnet 80 and the second magnetic member 60. The inspection magnet 80 is slidable relative to the first magnetic member 50 such that a gap 90 between the two can be variable. Finally, the inspection magnet 80 is slidable between a working position and a retracted position along the yoke 20.

In an embodiment, the yoke 20 includes a sleeve 10 and a piston 30. The sleeve 10 includes a working end 16, an upper end 15, and an open interior 11. In an embodiment, the inspection magnet 80 is slidable within the open interior 11. The working end 16 of the sleeve 10 may have an opening 19 such that a first surface 85 of the inspection magnet 80 may extend from or be flush with the working end 16 of the yoke 20. This allows the first surface 85 of the inspection magnet 80 to affix to a surface 101 of the work piece 100 when the working end 16 of the sleeve 10 is positioned against the surface 101 of the work piece 100. As shown in FIG. 3, when the inspection magnet 80 is located at the working end 16 of the sleeve 10 and its first surface 85 can affix to the work piece 100, the inspection magnet 80 is in its working position. When slid into the sleeve 10 and away from the working end 16, it is in its retracted position.

In an embodiment, the second magnetic member 60 is affixed to the inspection magnet 80 and the first magnetic member 50 is also slidable along the sleeve 10. As described above, the first magnetic member 50 may include a plurality of magnetic sources 51 forming a magnetic surface 55 with a first magnetic pattern 58. The second magnetic member 60 may be affixed to a second surface 86 of the inspection magnet 80 and include a plurality of magnetic sources 61. The magnetic sources 61 of the second magnetic member 60 may also form a magnetic surface 65 with a second magnetic pattern 68 thereon. The first magnetic pattern 58 may be complementary to the second magnetic pattern such that the magnetic surface 55 of the first magnetic member 50 attracts or repels the magnetic surface 65 of the second magnetic member 60.

In an embodiment, the magnetic surface 65 of the second magnetic member 60 is magnetically attracted to the magnetic surface 55 of the first magnetic member 50 when the first magnetic member 50 is rotated into first position relative to the second magnetic member 60. The magnetic surface 65 of the second magnetic member 60 may also be magnetically repelled from the magnetic surface 55 of the first magnetic member 50 when the first magnetic member 50 is rotated in a second position relative to the second magnetic member 60. The first magnetic pattern 58 and the second magnetic pattern 68 are complementary and attract or repel depending on the design of the two patterns when facing each other. In the first position, the patterns attract. In the second position, they repel.

To assist in removing the inspection magnet 80 from the surface 101 of the work piece 100, the strength of the magnetic field between the magnetic surfaces 55, 65 of the first and second magnetic members 50, 60 may be stronger than the strength of the magnetic field 88 between the first surface 85 of the inspection magnet 80 and the work piece 100. In particular, an attraction force between the first magnetic member 50 and second magnetic member 60 may be greater than an attraction force between the inspection magnet 80 and the work piece 100 when the first magnetic member 50 is in the first position relative to the second magnetic member 60 when the two magnetic surfaces 55, 65 are closely located.

In this embodiment, when the first magnetic member 50 is in the first position relative to the second magnetic member 60 and is positioned in close proximity thereto, the first magnetic member 50 is attracted to second magnetic member 60. The two are in proximity to one another when the gap 90 between the two is reduced such that the magnetic fields of the first magnetic member 50 and the second magnetic member 60 engage one another and/or overlap. The magnetic patterns 58, 68 along each of the first magnetic member 50 and second magnetic member 60 may be designed using the 3D printing process described below. The number and arrangement of magnetic pixels can be configured to provide a sufficiently strong magnetic field at a given proximity between the two patterns, and one that either attracts or repels depending on the relative orientations of each magnetic surface 55, 65.

Figure 4:
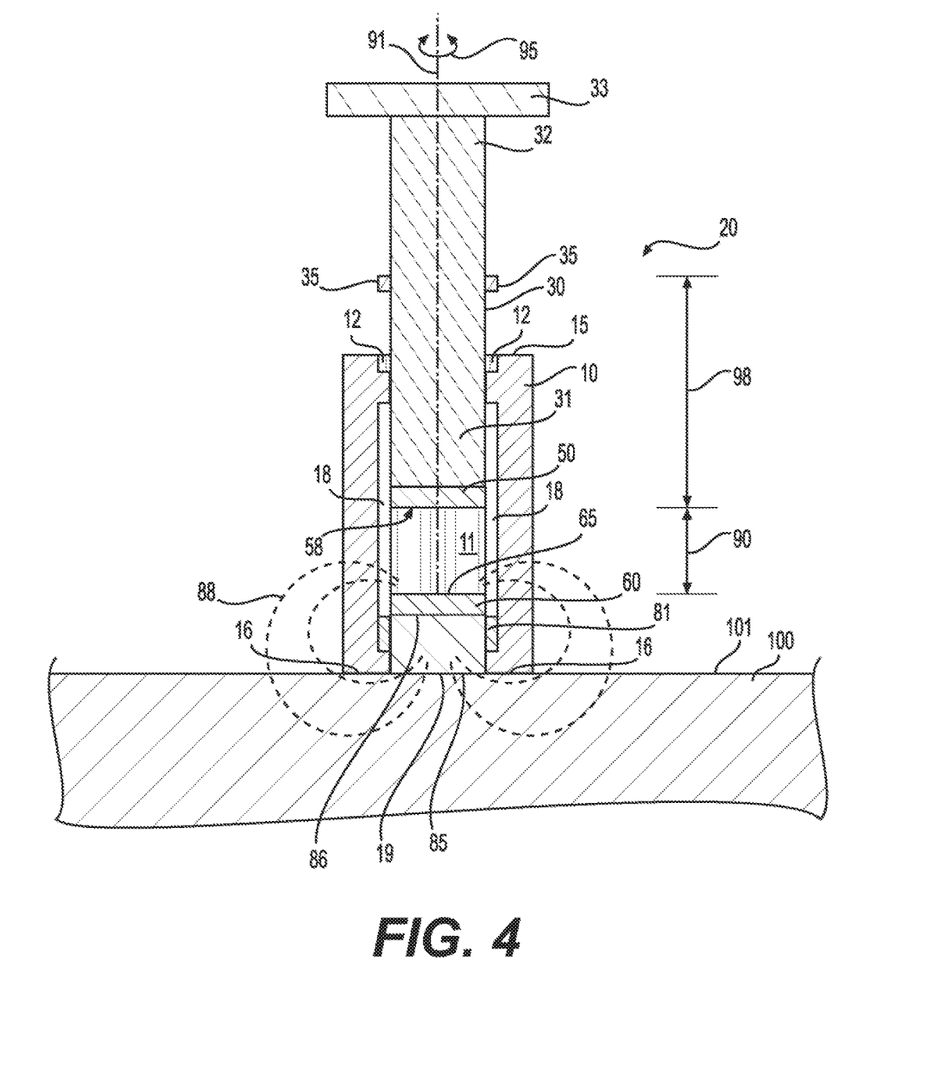
FIG. 4 is a cross-section view of an embodiment of the yoke of FIG. 3.

In an embodiment, the first magnetic member 50 is slidable along the sleeve 10 and is limited by a stop 35. In particular, the first magnetic member 50 is supported along a lower end 31 of the piston 30 and the travel of the piston 30 into the sleeve 10 is limited by the stop 35. The stop 35 may include a protrusion that is configured to contact an upper end 15 of the sleeve 10 and in some embodiments engage a notch 12 in the sleeve 10. The stop 35 limits a travel of the piston 30 in the sleeve 10 and prevents the lower end 31 of the piston 30 from sliding completely through the sleeve 10. This prevents the first magnetic member 50 from traveling completely through a length of the sleeve 10. In an embodiment and as illustrated in FIG. 4, the distance 98 between the magnetic surface 55 of the first magnetic member 50 and the stop 35 is such that the gap 90 is maintained between the first magnetic member 50 and the second magnetic member 60 when the stop 35 is in contact with the upper end 15 of the sleeve 10. Thus, the gap 90 between the first magnetic member 50 and the second magnetic member 60 is controlled along the working end 16 of the sleeve 10.

In this embodiment, the attraction force between the first magnetic member 50 and the second magnetic member 60 when the stop 35 is contacting the upper end 15 of the sleeve 10 may be greater than the attraction force between the inspection magnet 80 and the work piece 100. By controlling the gap 90, the inspection magnet 80 slides upwards towards the first magnetic member 50 and is removed from the work piece 100. This prevents the first magnetic member 50 from being drawn towards the second magnetic member 60 while the inspection magnet 80 remains affixed to the work piece 100.

Figure 5:
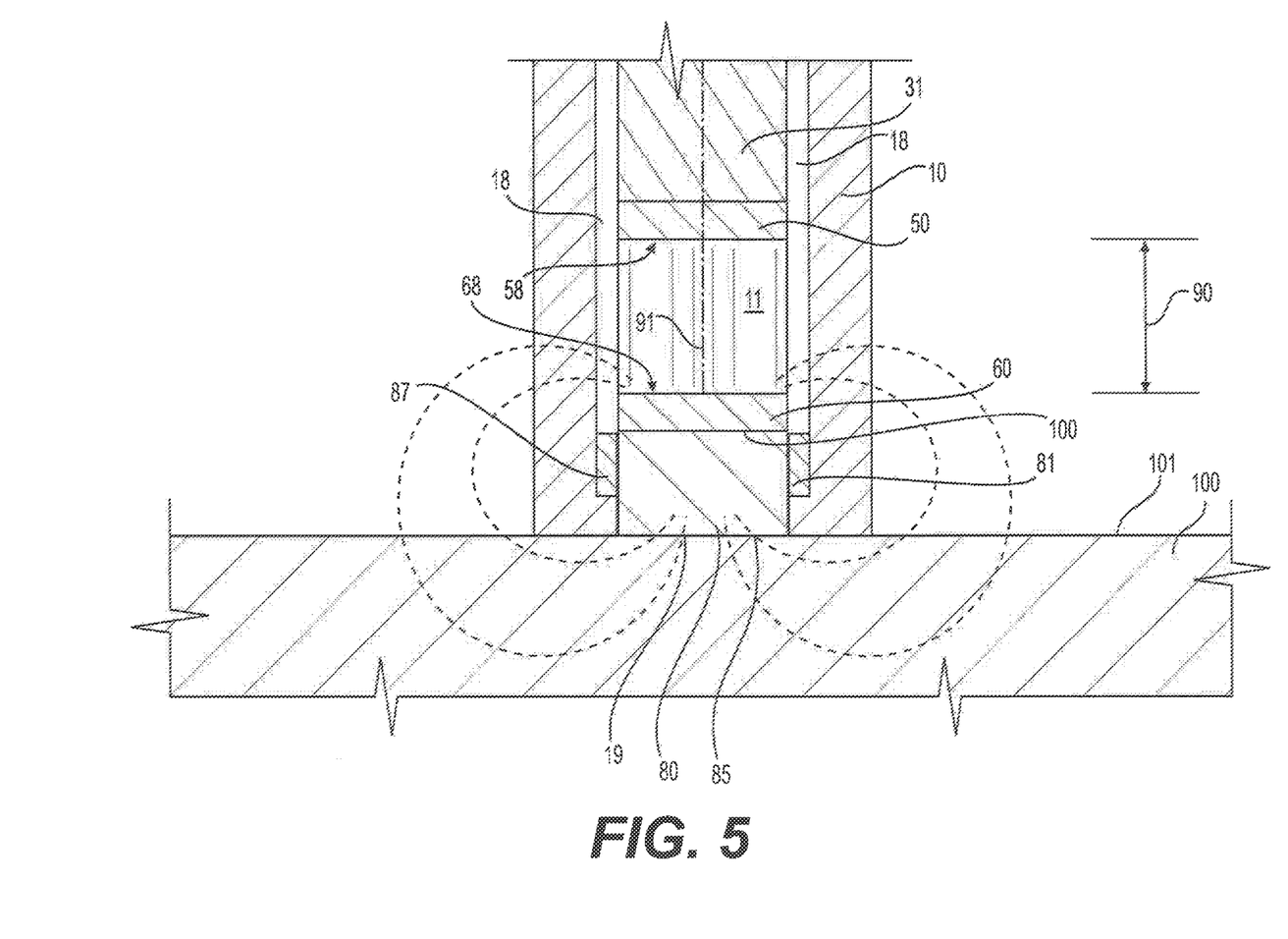
FIG. 5 is a cross-section view of the working end of the embodiment in FIG. 4.

In an embodiment, the piston 30 is rotatable within the sleeve 10 and can rotate the first magnetic member 50 between the first position and second position. In addition, as shown in FIGS. 4 and 5, the sleeve may also include one or more grooves 18 extending along a longitudinal axis 91 of the interior 11. The grooves 18 are configured to receive a flange 81 extending from the inspection magnet 80. The groove 18 accepts the flange 81 therein and allows the flange 81 to slide along the groove 18. The groove 18 also captures the flange 81 and prevents rotation of the inspection magnet 80 within the sleeve 10. The inspection magnet 80 may have one or more flanges 81 and the sleeve 10 may have one or more grooves 18. Thus, the inspection magnet 80 is slidable in the sleeve 10 and does not rotate relative to the sleeve 10 in this embodiment. This prevents the inspection magnet 80 from undergoing unwanted rotation and thus misaligning the first inspection magnet 50 and second inspection magnet 60.

Referring to FIGS. 2-5, the yoke 20 may further include a handle grip 33 along an upper end 32 of the piston 30 while the first magnetic member 50 is affixed to the lower end 31 of the piston 30. Thus, the handle grip 33 is coupled to the first magnetic member 50. In addition, an enlarged stop 34 may be provided below the handle grip 33 extending through the piston 30. The piston is slidable and rotatable relative to the sleeve 10 to position and rotate the first magnetic member 50 relative to the second magnetic member 60. The second magnetic member 60 is affixed to the inspection magnet 80, which is also slidable within the sleeve 10. This allows the magnetic patterns 58, 68 to be moved close to one another and aligned to attract or repel the first magnetic member 50 to or from the second magnetic member 60.

In an embodiment, the magnetic surface 55 of the first magnetic member 50 is disposed on a first surface 59 of the first magnetic member 50, and the magnetic surface 65 of the second magnetic member 60 is disposed on a second surface 67 of the second magnetic member 60. The first surface 59 may include a lower surface of the first magnetic member 50 and the second surface 67 may include an upper surface of the second magnetic member 60. The first magnetic member 50 and second magnetic member 60 may be coaxial along the longitudinal axis 91 of the sleeve 10 and face one another. When facing one another, the magnetic surface 55 of the first magnetic member 50 may be parallel to the magnetic surface 65 of the second magnetic member 60. Additionally, when the first magnetic member 50 and the second magnetic member 60 come into proximity to one another, the attractive or repulsive forces of the magnetic patterns 58, 68 act to attract or repel the two together or apart.

In an embodiment, the first magnetic member 50 and the second magnetic member 60 are rounded members having a rounded outer profile 56, 66, a first surface 59, 69, and a second surface 57, 67. The magnetic material is printed on or through the cross section 52, 62 of the rounded members and the poles of the magnetic material form the magnetic patterns 58, 68 along the first surface 59 of first magnetic member 50 and second surface 67 of the second magnetic member 60.

In an embodiment, the plurality of magnetic sources 51 of the first magnetic member 50 include an array of alternating magnetic poles along the first surface 59 forming the first magnetic pattern 58. The plurality of magnetic sources 61 of the second magnetic member 60 include an array of alternating magnetic poles along a second surface 67 with the second magnetic pattern 68. The first magnetic pattern 58 is complementary to the second magnetic pattern 68 when the first magnetic member 50 is in the first rotational position, such that the array of alternating magnetic poles of the first magnetic member 50 is attracted to the array of alternating magnetic poles of the second magnetic member 60. In addition, the first magnetic pattern 58 mirrors the second magnetic pattern 68 when the first magnetic member 50 is in the second rotational position, such that the array of alternating magnetic poles of the first magnetic member 50 is repelled from the array of alternating magnetic poles of the second magnetic member 60.

The arrangement of the magnetic sources 51, 61 (i.e. the magnetic pixels) alternates positive and negative poles along each magnetic surface 55, 65. The alternating pattern may include several positive poles adjacent to other positive poles, and several negative poles adjacent to other negative poles. The alternating arrangement define the patterns 58, 68 so the two magnetic surfaces 55, 65 attract and repel each other depending on their relative rotational angle when facing one another and in close proximity.

In one embodiment, the first surface 59 of the first magnetic member 50 and the second surface 67 of the second magnetic member 60 are configured to mate against one another when the array of alternating magnetic poles (i.e. the first magnetic pattern 58) of the first magnetic member 50 is attracted to the array of alternating magnetic poles (i.e. the second magnetic pattern 68) of the second magnetic member 60. In other embodiments, the first surface 59 and the second surface 67 are configured to maintain a minimum air gap between the two when the array of alternating magnetic poles of the first magnetic member 50 is attracted to the array of alternating magnetic poles of the second magnetic member 60. In this embodiment, the first magnetic pattern 58 both repels and attracts the second magnetic pattern 68 when the first magnetic member 50 is in the first rotational position. Thus, an air gap is maintained between the two while at the same time the two are attracted to one another. The two can thus slide within the sleeve 10 without contacting each other.

Figure 6:
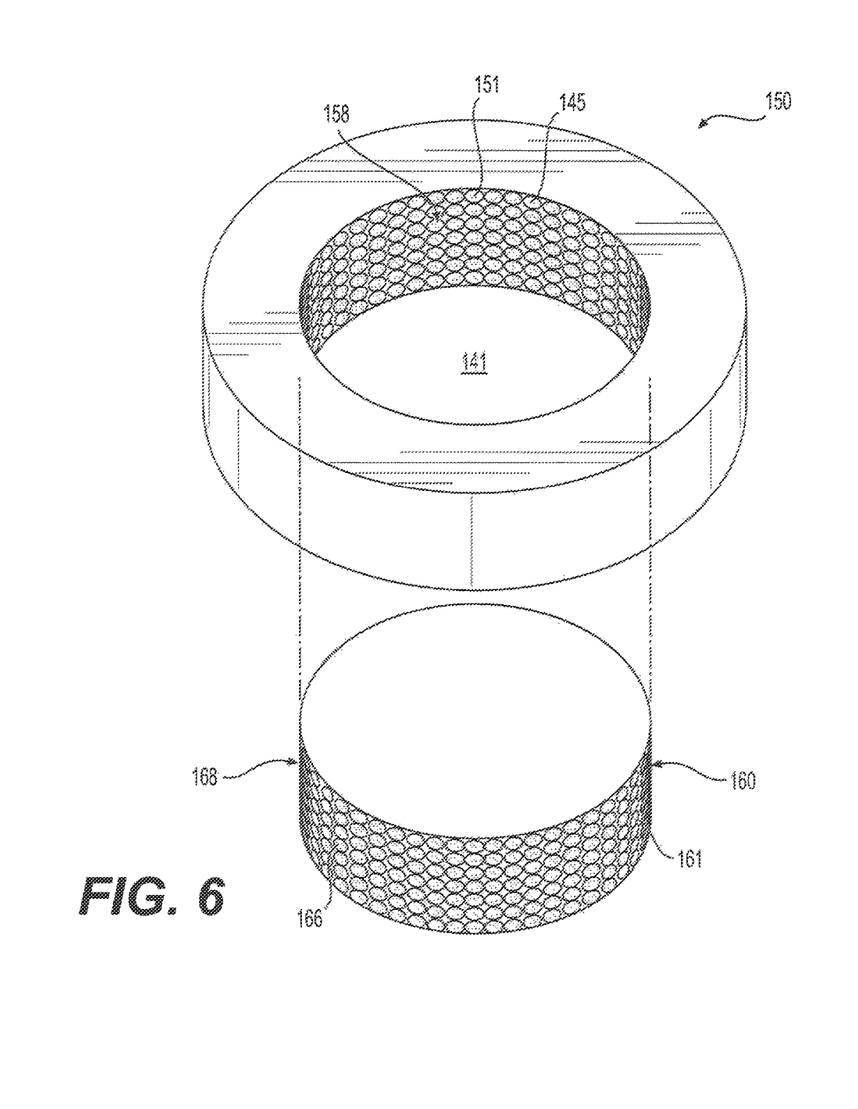
FIG. 6 is an embodiment of the first and second magnetic member of the present disclosure.

Referring now to FIG. 6, there is shown an embodiment of the first and second magnetic members. In an embodiment, the first magnetic member 50 forms a ring 150 and the second magnetic member 60 forms a rounded member 160 configured to be received within an open interior 141 of the ring 150. Alternatively, the second magnetic member 60 may form a ring 150 and the first magnetic member 50 may form a rounded member 160 configured to be received within an open interior 141 of the ring 150. In this arrangement, the ring 150 has an interior surface 145 that is a magnetic surface including a plurality of magnetic sources 151 forming a magnetic pattern 158 thereon. The rounded member 160 has an outer surface 166 that is a magnetic surface including a plurality of magnetic sources 161 forming a magnetic pattern 168 thereon. The ring 150 may support the first magnetic pattern 158 or the second magnetic pattern 168. Likewise the rounded member 160 may support the first magnetic pattern 158 or the second magnetic pattern 168.

INDUSTRIAL APPLICABILITY

The disclosed magnetic particle inspection tool may be applicable to any ferromagnetic work piece requiring inspection. The disclosed magnetic particle inspection tool may allow for a yoke having a shorter height than traditional inspection tools, making it more suitable for application in confined areas. Moreover, the magnetic particle inspection tool may also improve the ability of the user to remove the tool from a work piece once the inspection magnet has affixed thereto. The operation of magnetic particle inspection tool using a first and second yoke will now be explained.

3D printing magnets involves a layering process in which magnetic material is layered to form a magnetic surface with a plurality of magnetic sources thereon. The magnetic sources may be printed on the surface of an object or through its cross section. Each magnetic source has an upper end along the magnetic surface, the upper end having a polarity. When collectively arranged on the magnetic surface, each magnetic source forms a "pixel" with its own polarity along the magnetic surface. By specifically arranging the polarities of the magnetic sources across a magnetic surface, a magnetic pattern is formed. The magnetic pattern can be designed to function in combination with a complementary pattern on a second magnetic surface, the two patterns dictating when the two magnetic surfaces attract and when they repel based on their relative patterns. The patterns can be designed such that when the two magnetic surface face one another, at certain orientations the two surfaces attract, and at others they repel. Thus, the pattern controls when the two surfaces attract and repel, and the rotation of one surface relative to the other can switch the surfaces between attraction and repulsion.

The magnetic particle inspection tool of the present disclosure may be used by first placing the sleeve of a first yoke against a work piece 100. The magnetic particle inspection tool includes a piston 30 slidable within the sleeve 10 and coupled to the first magnetic member 50. The inspection magnet 80 is configured to magnetize the work piece 100 when a first surface 85 is attached to the work piece 100. The first magnetic member 50 is rotatable relative to the inspection magnet 80 between a first position and a second position. The inspection magnet 80 is slidable within the sleeve 10 and relative to the first magnetic member 50. The inspection magnet 80 is positioned along the working end 16 of the sleeve 10 such that its first surface 85 can affix to the surface 101 of the work piece 100.

Once the inspection magnet 80 of the first yoke is affixed to the work piece 100, a second yoke may be affixed to another location along the work piece 100. Ferrous particles can be spread on the work piece 100 between the first yoke and second yoke. The particles may be distributed in powder form or in an aqueous suspension. The yokes magnetize the work piece 100 and the particles align within discontinuities along the surface 101 of the work piece 100. Thus, flaws can be identified and addressed.

To remove the yokes from the work piece 100, the inspection magnet 80 is retracted into the sleeve 10. As described above, the first magnetic member 50 includes a plurality of magnetic sources 51 forming a magnetic surface 55 with a first magnetic pattern 58 thereon. The second magnetic member 60 is affixed to a second surface 86 of the inspection magnet 80 or is an integral portion thereof. The second magnetic member 60 includes a plurality of magnetic sources 61 forming a magnetic surface 65 with a second magnetic pattern 68 thereon. The magnetic surface 65 of the second magnetic member 60 is magnetically attracted to the magnetic surface 55 of the first magnetic member 50 when the first magnetic member 50 is rotated into the first position and placed in close proximity to the second magnetic member 60. To retract the inspection magnet 80 affixed to the work piece 100, the attraction force between the first magnetic member 50 and second magnetic member 60 may be greater than the attraction force between the inspection magnet 80 and the work piece 100 when the first magnetic member 50 is in the first position and is in proximity to the second magnetic member 60.

Thus, the magnetic attraction between the first magnetic member 50 and second magnetic member 60 overcomes the attraction of the inspection magnet 80 to the work piece 100. This allows the inspection magnet 80 to be withdrawn from the work piece by rotating the piston 30 and/or the first magnetic member 50. This eliminates the need to pull the inspection magnet 80 or yoke from the work piece 100.

To position the inspection magnet 80 against the work piece 100 at another location after being withdrawn into the sleeve 10, the magnetic surface 65 of the second magnetic member 60 is configured to magnetically repel from the magnetic surface 55 of the first magnetic member 50 when the first magnetic member 50 is rotated into the second position. This repels the inspection magnet 80 from the first magnetic member 50 and the inspection magnet 80 can then be positioned along the working end 16 of the sleeve 10. To facilitate separation, the second magnetic member 60 and/or the inspection magnet 80 may be secured by the sleeve 10 such that they cannot rotate in the sleeve 10 as the first magnetic member 50 rotates. Likewise, the travel of the piston 30 and/or the first magnetic member 50 may be limited within the sleeve 10 such that the first magnetic member 50 and second magnetic member 60 cannot come into contact while the inspection magnet 80 is disposed within the working end 16 of the sleeve (i.e. while contacting the work piece 100).

It will be apparent to those skilled in the art that various modifications and variations can be made to the magnetic particle inspection tool. Other embodiments will be apparent to those skilled in the art from consideration of the specification and practice of the disclosed magnetic particle inspection tool. It is intended that the specification and examples be considered as exemplary only, with a true scope being indicated by the following claims and their equivalents.

What is claimed is:

1. A magnetic particle inspection tool, comprising:
   a yoke including:
      an inspection magnet and a first magnetic member;
      the inspection magnet being configured to magnetize a work piece when a first surface is attached to the work piece;
      the first magnetic member being rotatable relative to the inspection magnet between a first position and a second position;
      the inspection magnet being slidable relative to the first magnetic member;
      the first magnetic member including a plurality of magnetic sources forming a magnetic surface with a first magnetic pattern;
      a second magnetic member affixed to a second surface of the inspection magnet, the second magnetic member including a plurality of magnetic sources forming a magnetic surface with a second magnetic pattern thereon;

the magnetic surface of the second magnetic member being magnetically attracted to the magnetic surface of the first magnetic member when the first magnetic member is in the first position; and the magnetic surface of the second magnetic member being magnetically repelled from the magnetic surface of the first magnetic member when the first magnetic member is in the second position.

2. The magnetic particle inspection tool of claim 1, wherein:

the plurality of magnetic sources of the first magnetic member and the second magnetic member are 3D printed magnetic sources.

3. The magnetic particle inspection tool of claim 1, wherein:

the yoke further includes a sleeve with a working end;

the inspection magnet being slidable within the sleeve between a working position and a retracted position;

wherein the inspection magnet is disposed along the working end of the sleeve when in the working position.

4. The magnetic particle inspection tool of claim 1, wherein:

the magnetic surface of the first magnetic member is coaxial with the magnetic surface of the second magnetic member.

5. The magnetic particle inspection tool of claim 1, further including a handle grip coupled to the first magnetic member.

6. The magnetic particle inspection tool of claim 1, wherein:

the yoke further includes a sleeve and the first magnetic member is slidable within the sleeve.

7. The magnetic particle inspection tool of claim 6, further including:

a piston slidable within the sleeve and coupled to the first magnetic member;

the piston having an upper end that includes a handle grip.

8. The magnetic particle inspection tool of claim 7, wherein:

the sleeve further includes a stop that is configured to contact the piston and limit a travel of the piston within the sleeve;

the stop preventing the first magnetic member from contacting the second magnetic member and forming a gap therebetween when the inspection magnet and the yoke are in contact with the work piece.

9. The magnetic particle inspection tool of claim 8, wherein:

an attraction force between the first magnetic member and second magnetic member is sufficient to draw the inspection magnet across the gap and away from the work piece when the first magnetic member is in the first position and the piston is in contact with the stop.

10. The magnetic particle inspection tool of claim 6, wherein:

the sleeve further includes one or more grooves configured to receive a flange extending from the inspection magnet, the groove extending along a longitudinal axis of the sleeve and the flange being slidable within the groove.

11. The magnetic particle inspection tool of claim 6, wherein:

the first magnetic member further includes a ring with an open interior and an interior surface, the magnetic surface of the first magnetic member being disposed on the interior surface; and the second magnetic member further including a rounded member with an outer surface, the magnetic surface of the second magnetic member being disposed on the outer surface.

12. The magnetic particle inspection tool of claim 1, wherein:

an attraction force between the first magnetic member and the second magnetic member is greater than an attraction force between the inspection magnet and the work piece when the first magnetic member is in the first position.

* * * * *